US00PP29585P2

(12) United States Plant Patent
Carter

(10) Patent No.: US PP29,585 P2
(45) Date of Patent: Aug. 7, 2018

(54) ***SALVIA* PLANT NAMED 'RHYTHM AND BLUES'**

(50) Latin Name: *Salvia x guaranitica*
Varietal Denomination: Rhythm and Blues

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 15/731,749

(22) Filed: Jul. 27, 2017

(51) Int. Cl.
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para
(74) *Attorney, Agent, or Firm* — Bethany R. Roahrig; Barbara Campbell; Cochran Freund & Young LLC

(57) ABSTRACT

A new cultivar of *Salvia* named 'Rhythm & Blues' that is distinguishable by large flowers which are intense deep-purple in color, which are borne in profusion on naturally branching plants with season-long deep green foliage is disclosed.

2 Drawing Sheets

Genus and species: *Salvia* x *guaranitica*.
Variety denomination: 'Rhythm & Blues'.

BACKGROUND

The present disclosure relates to a new and distinct cultivar of *Salvia* plant, also known as a sage, a perennial that is grown for use as an ornamental landscape and container plant. The new variety is known botanically as *Salvia* x *guaranitica* and will be referred to hereinafter by the cultivar name 'Rhythm & Blues'.

'Rhythm & Blues' was selected in 2015 from a population of seedlings which the inventor raised from seed collected from plants resulting from the controlled hybridization between a plant of *Salvia* x *guaranitica* var *violacea* (species, unpatented) as male parent, and a plant of *Salvia* x *guaranitica* var *purpurea* (species, unpatented) as female parent. The hybridization and selection was carried out by the inventor at the inventor's nursery in Elk, Calif.

'Rhythm and Blues' was selected by the inventor for its combination of flower count, flower size, intensity of flower color, deep green foliage and naturally compact and branching plant habit.

'Rhythm & Blues' was first asexually propagated in 2015 in a greenhouse at the inventor's nursery in Elk, Calif. using softwood tip cuttings. The inventor has determined during successive cycles of asexual propagation that 'Rhythm & Blues' is stable and reproduces true to type.

SUMMARY

The following traits have been repeatedly observed and represent the distinguishing characteristics of 'Rhythm & Blues'. 'Rhythm & Blues' has not been tested under all possible conditions and phenotypic differences may be observed with variations in environmental, climatic, and cultural conditions, without however, any variance in genotype.

1. 'Rhythm & Blues' exhibits a compact well-branched upright plant habit;

2. The flowers of 'Rhythm & Blues' are vibrant violet-blue in color;
3. 'Rhythm & Blues' grows and flowers rapidly. Flowering plants may be produced in 10 to 12 weeks from a cutting.
4. The calyces of the flowers of 'Rhythm & Blues' range in color from very dark purple to black. The calyces are black in conditions of full sunlight.
5. 'Rhythm & Blues' produces new flowering stems continuously from spring to fall.
6. The foliage of 'Rhythm & Blues' is dark green in color at all stages of growth.
7. The leaves of 'Rhythm & Blues' are thick and robust.

DESCRIPTION OF THE PHOTOGRAPHS

The accompanying color photographs illustrate the overall appearance of the new *Salvia* cultivar 'Rhythm & Blues' showing the colors as true as it is reasonably possible to obtain in colored reproductions of this type. The photographs were taken in spring and summer 2017 from plants which were growing out of doors in Oxnard, Calif. The plants had received one pinch after initial cutting establishment. Colors in the photographs may differ from the color values cited in the detailed botanical description, which more accurately describes the actual colors of the new variety 'Rhythm & Blues'.

DESCRIPTION OF THE NEW VARIETY

Figure 1:
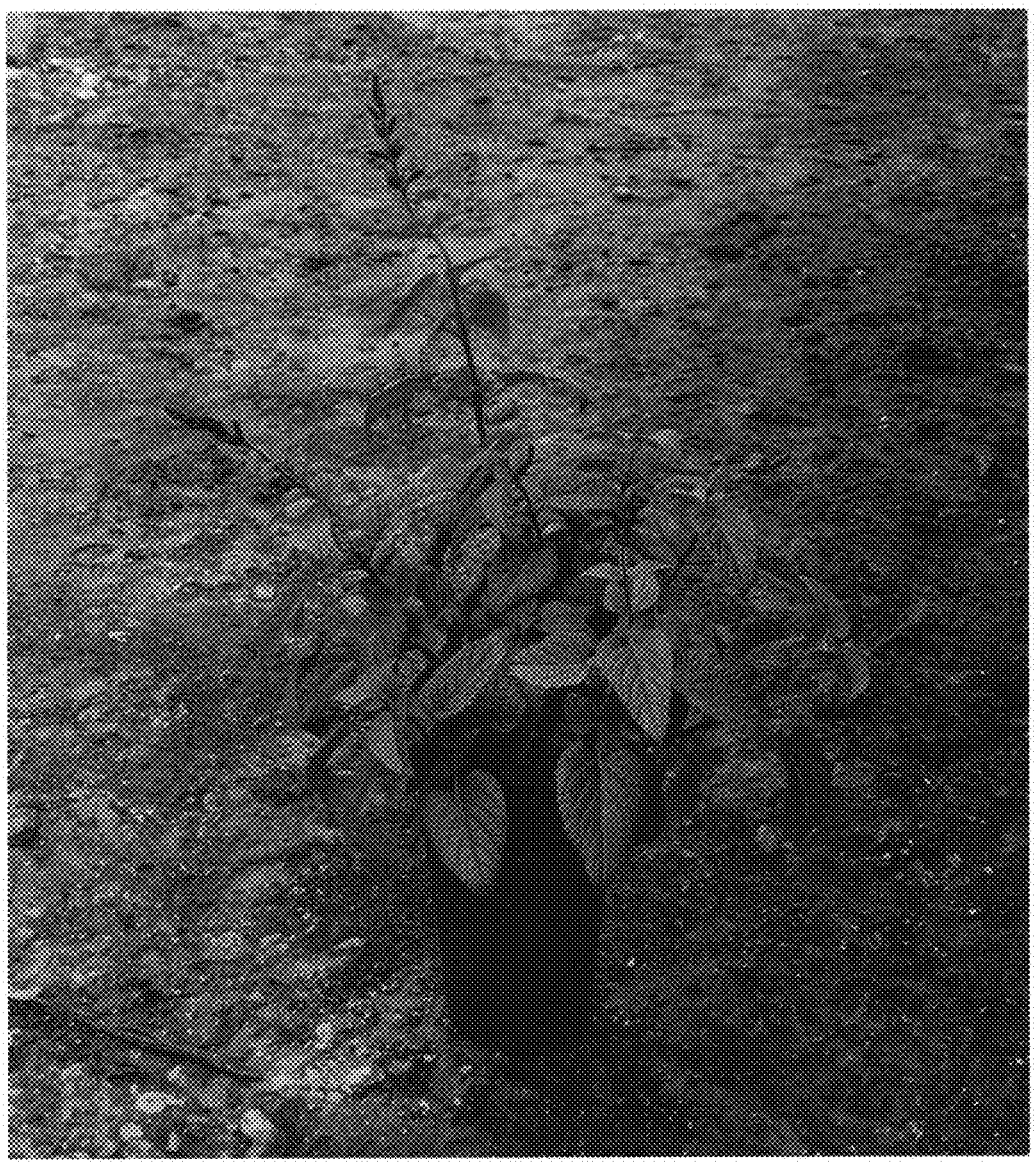
FIG. 1 depicts an entire plant of 'Rhythm & Blues' as the first flowering stems develop.
Figure 2:
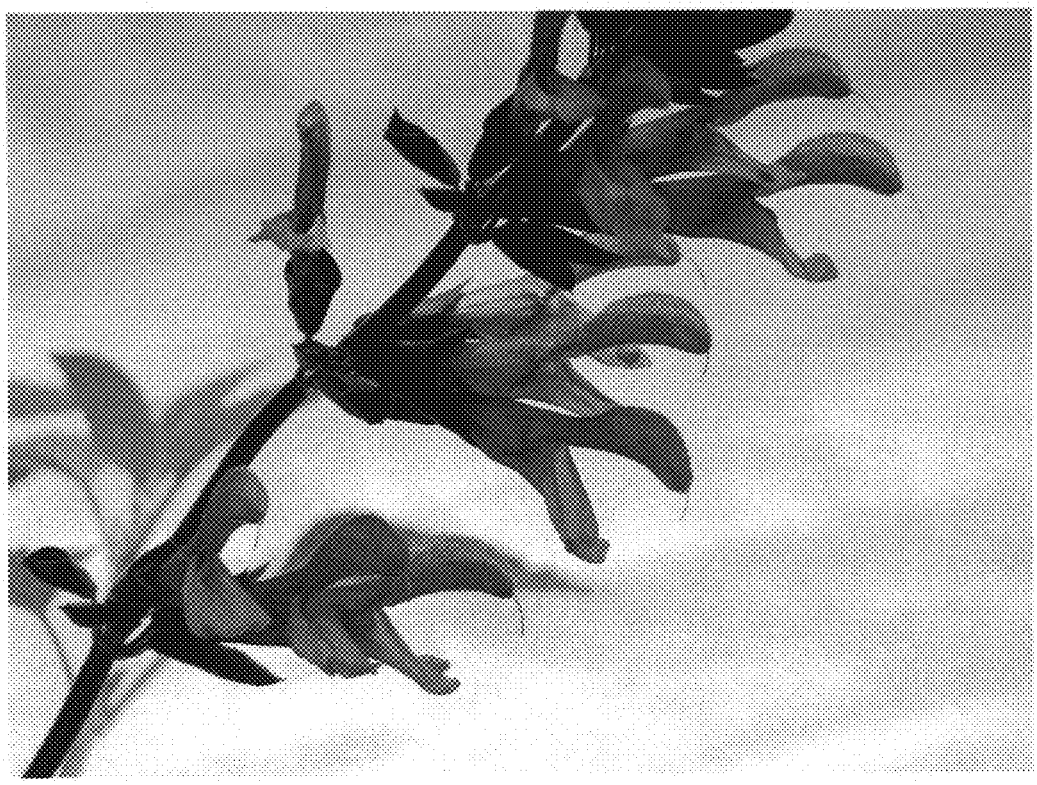
FIG. 2 depicts a close-up view of the inflorescence of 'Rhythm & Blues'.

The following detailed descriptions set forth the distinctive characteristics of 'Rhythm & Blues'. Observations, measurements, values, and comparisons were collected in March, April and July 2017 in Santa Barbara, Calif. from three to six-month old plants grown outdoors in full sun. Color determinations have been made in accordance with The 2007 Royal Horticultural Society Colour Chart from London England, except where general color terms of ordinary dictionary significance are used.

Classification:

*Family*.—Lamiaceae.
*Genus*.—*Salvia*.
*Species*.—x *guaranitica*.
*Common name*.—Sage.

Parentage:

*Female parent*.—*Salvia* x *guaranitica* var *purpurea*.
*Male parent*.—*Salvia* x *guaranitica* var *violacea*.

Plant:

*Propagation method*.—Softwood tip cuttings.
*Rooting system*.—Fine and fibrous.
*Vigor*.—Moderate vigor.
*Time to develop roots*.—5 days are needed for a cutting to develop roots at recommended rooting temperature of 20° to 22° Centigrade.
*Crop time*.—Approximately 12 weeks are required to produce a budded and flowering plant in a one gallon container from a rooted cutting.
*Suggested container size*.—Quart to 1 gallon container.
*Use*.—Ornamental for use as a landscape plant or container plant.
*Type*.—Perennial.
*Overall dimensions*.—After one year's growth in a 3.5 inch container: 45 cm to 50 cm in height, including the inflorescence, and 18 cm to 24 cm in width.
*Cultural requirements*.—Grow in full sun with moderate water and well-draining soil.
*Hardiness*.—USDA Zone 7.
*Form*.—Bush.
*Growth habit*.—Compact.
*Blooming season*.—From one month after breaking spring dormancy to first frost.
*Lastingness of blooms*.—Inflorescence has some flower for 14 days, individual flowers last for 2 to 3 days.

Stem:

*Length*.—15 cm to 20 cm.
*Width*.—5 mm to 8 mm.
*Color*.—187A (at base) to N186A.
*Shape*.—Square, edges rounded.
*Texture*.—Suffruticose.

Branches:

*Quantity*.—4 to 6.
*Length* (*to base of raceme*).—18 cm to 25 cm.
*Width*.—4 mm.
*Internode length*.—1.5 cm to 2.5 cm.
*Color*.—186A.
*Shape*.—Square.
*Texture*.—Smooth.

Leaves:

*Type, arrangement*.—Simple, opposite.
*Attachment*.—Petiolate.
*Quantity per branch*.—6 to 8 pairs.
*Shape*.—Deltoid.
*Length*.—9 cm.
*Width*.—7 cm.
*Margin*.—Weakly undulating, prominently dentate. Teeth 3 mm to 5 mm apart, 1.5 mm to 2 mm in depth.
*Thickness*.—Thick, stiff.
*Venation*.—Pinnate. Veins (adaxial surface): Depressed, color as leaf except midrib, 151A. Veins (abaxial surface): Raised, color 145C.
*Texture* (*both surfaces*).—Pubescent, hairs very fine, color hard to match, lighter than N187D.
*Color*.—Adaxial surface: 137A. Abaxial surface: 137C.
*Apex*.—Acute.
*Base*.—Hastate.
*Fragrance*.—Pleasant sage fragrance when rubbed.
*Stipules*.—Present in pairs at each leaf axil. Small, sessile, elliptic, 7 mm to 8 mm in length, 3 mm in width. All other characteristics same as leaves.

Petiole:

*Shape*.—Terete, adaxial channel.
*Length*.—4 cm.
*Width*.—2 mm.
*Texture*.—Puberulent.
*Color*.—178A except 151A within channel.

Peduncle:

*Length* (*to first flower whorl*).—5 cm to 8 cm.
*Length* (*to uppermost flower whorl*).—25 cm to 30 cm.
*Shape*.—Square.
*Width*.—4 mm to 6 mm.
*Texture*.—Puberulent.
*Color*.—Ranges between N186A and 203B.

Inflorescence:

*Type*.—Terminal raceme.
*Length*.—20 cm to 25 cm.
*Diameter*.—7 cm.
*Flower arrangement*.—Flowers are arranged in whorls.
*Quantity of flowers*.—A range of 4 to 12 flowers per whorl and up to 13 whorls per raceme.
*Distance between whorls*.—1.0 cm. to 2.5 cm.
*Flowering season*.—Year round in Southern California and spring to summer elsewhere.
*Lastingness of the flowers* (*on the plant*).—From 8 days in spring to 3 days in summer.

Pedicel:

*Length*.—6 cm.
*Width*.—1 mm.
*Texture*.—Puberulent.
*Color*.—Ranges between N186A and 203B.

Calyx:

*Shape*.—Campanulate, flared toward the apex.
*Length*.—12 mm to 15 mm.
*Width*.—5 mm.

Sepals:

*Quantity*.—2, one upper, one lower, substantially longitudinally fused.
*Length*.—12 mm to 15 mm. of which 4 mm to 5 mm free.
*Width*.—8 mm when flattened.
*Shape*.—Boat shaped.
*Apex*.—Acuminate.
*Base*.—Truncate.
*Margin*.—Entire.
*Texture*.—Adaxial surface: Puberulent, longitudinally ribbed. Ribs 1 mm apart, raised less than 0.1 mm. Abaxial surface: Glabrous, longitudinal depressions.
*Color*.—Ranges between N186A and 203B.

Flowers:

*Quantity*.—From 4 to 12 flowers per whorl and up to 13 whorls per flowering stem.
*Shape*.—Tubular, two-lipped.
*Length*.—5.5 cm to 6.0 cm.
*Width*.—10 mm to 12 mm.

*Height* (*across extremities of upper and lower lip*).—2.0 cm to 2.5 cm.

*Fragrance*.—Pleasant sage fragrance.

Bud (as emerges from calyx):

*Shape*.—Ellipsoidal.

*Length*.—4 mm to 5 mm.

*Width*.—3 mm to 4 mm.

*Texture*.—Pubescent, especially apex which already bears cluster of hairs of upper petal lip.

*Color*.—95B.

Corolla:

*Shape*.—Tubular.

*Length*.—2 cm.

*Width*.—3 mm.

*Texture*.—Glabrous.

*Color* (*both surfaces*).—99C.

Petals:

*Quantity*.—2.

*Arrangement*.—One upper petal appearing as a hood, and one lower petal which appears as a large prominent lip.

*Upper petal*.—Aspect: Horizontal to slightly elevated. Shape: Hood. Length: 5.5 cm to 6.0 cm (including corolla tube). Width: 10 mm to 12 mm. Texture: Adaxial surface: Corolla tube glabrous, hood puberulent, hairs 0.5 mm to 1.0 mm in length, color 99A. Abaxial surface: Glabrous, with two longitudinal ribs. Apex: Rounded. Base: Truncate with lower lip at corolla mouth. Margin: Smooth, entire. Color (both surfaces): 95B to 99B.

*Lower petal, lip*.—Aspect: Downward, between 30° and 45° below horizontal. Shape: Rhomboid, concave. Length: 15 mm to 20 mm (free of upper petal). Width: 10 mm to 12 mm. Texture: Adaxial surface: Smooth. Abaxial surface: Smooth, glabrous, semi-glossy. Apex: Emarginate, depth of notch 1.5 mm. Base: Truncate. Margin: Gently undulating. Color (both surfaces): 95B to 99B.

*Floral bracts*.—Arrangement: Occasionally present in opposite pairs at base of flower. Shape: Ovate. Length: 2 mm to 4 mm. Width: 2 mm. Color (both surfaces): 85D. Apex: Acuminate. Margin: Entire. Persistence: Bracts are not persistent.

Reproductive organs:

*Stamens*.—Quantity: 2, connected to corolla tube wall, fused at base. Length: 6.5 cm of which 8 mm to 10 mm exserted from flower (upper lip) apex. Color: 85D, 94C where exserted.

*Filament*.—Length: 3 cm, 5 cm to 6 cm in length. Color: 85D.

*Anther*.—Shape: Narrowly elliptical, dorsifixed off-center. Length: 4 mm. Width: 0.5 mm to 1.0 mm. Color: 90A.

*Pollen*.—Amount: Sparse. Color: 163B.

*Pistil*.—Quantity: 1. Stigma: Shape: Asymmetrically forked. Length: Longer fork 12 mm, strongly recurved; shorter fork 10 mm, gently recurved. Width: 0.5 mm. Color: 90B. Style: Length: 9 cm. Color: 85D.

*Ovary* (*only observed unfertilized, one pair of immature achenes*).—Length: 3 mm. Width: 1.5 mm. Color: 10B, achenes 8A.

*Seed*.—Shape: Ovoid. Dimensions: 3 mm in length, 1.5 mm in diameter. Color: 199A to 199B. Surface: Rough.

Disease and pest susceptibility: Susceptible to sucking insects when stressed. Generally outgrows most bacterial and viral infections. Resistant to deer and rabbit grazing.

Drought tolerance: Drought tolerant.

COMPARISON WITH PARENTAL LINES AND KNOWN VARIETY

'Rhythm & Blues' is distinguishable from each of its parents by the color and texture of its foliage which is deeper green and thicker than either parent and by the larger size and quantity and the deeper and more intense color of its flowers.

The variety of *Salvia* x *guaranitica* which the inventor considers to be most similar to 'Rhythm & Blues' is *Salvia* 'Black and Blue' (unpatented). In comparison with 'Black and Blue', 'Rhythm & Blues' exhibits thicker and darker green foliage and larger flowers borne in greater profusion and more intensely deep purple in color. The foliage of 'Black and Blue' is prone to yellowing as the season proceeds. The flowers of 'Black & Blue' are blue-purple in color.

I claim:

1. A new and distinct cultivar of *Salvia* plant named 'Rhythm & Blues' as described and illustrated herein.

* * * * *